US008455200B2

(12) United States Patent
Puskas et al.

(10) Patent No.: US 8,455,200 B2
(45) Date of Patent: Jun. 4, 2013

(54) MEASUREMENT OF PKA FOR CANCER DETECTION

(75) Inventors: Robert Puskas, Manchester, MO (US); Douglas Held, Ballwin, MO (US)

(73) Assignee: Traxxsson, LLC, St. Louis, MO (US)

( * ) Notice: Subject to any disclaimer, the term of this patent is extended or adjusted under 35 U.S.C. 154(b) by 161 days.

(21) Appl. No.: 12/904,737

(22) Filed: Oct. 14, 2010

(65) Prior Publication Data

US 2012/0322080 A1 Dec. 20, 2012

Related U.S. Application Data

(60) Provisional application No. 61/251,769, filed on Oct. 15, 2009.

(51) Int. Cl.
*C12Q 1/68* (2006.01)

(52) U.S. Cl.
USPC ..... 435/6.14; 435/9.94; 424/146.1; 424/94.1; 436/813

(58) Field of Classification Search
None
See application file for complete search history.

(56) References Cited

U.S. PATENT DOCUMENTS

| | | | |
|---|---|---|---|
| 5,869,275 | A | 2/1999 | Huang |
| 2002/0068036 | A1 | 6/2002 | Hevezi et al. |
| 2003/0108907 | A1 | 6/2003 | Rosen et al. |
| 2004/0086910 | A1 | 5/2004 | O'Brien et al. |
| 2004/0086916 | A1 | 5/2004 | Farnham et al. |
| 2005/0272067 | A1 | 12/2005 | Macina et al. |
| 2006/0160090 | A1 | 7/2006 | Macina et al. |
| 2006/0204956 | A1 | 9/2006 | Kipreski et al. |
| 2007/0042420 | A1 | 2/2007 | Farnham et al. |
| 2007/0128593 | A1 | 6/2007 | Petroziello et al. |
| 2008/0213918 | A1 | 9/2008 | Feder et al. |
| 2008/0305558 | A1 | 12/2008 | Loveday et al. |
| 2009/0061432 | A1 | 3/2009 | Hoelz et al. |
| 2010/0248269 | A1 | 9/2010 | Small-Howard |

FOREIGN PATENT DOCUMENTS

| | | |
|---|---|---|
| EP | 1874823 | 9/2008 |
| WO | 9841649 A2 | 9/1998 |
| WO | 0129056 A1 | 4/2001 |
| WO | 0216939 A2 | 2/2002 |
| WO | 03065873 A2 | 8/2003 |
| WO | 2004092338 A2 | 10/2004 |
| WO | 2009087462 A2 | 7/2009 |

OTHER PUBLICATIONS

Wang H et al. Extracellular Activity of Cyclic AMP-Dependent Protein Kinase as a Biomarker for Human Cancer Detection: Distribution Characteristics in a Normal Population and Cancer Patients, Cancer Epidemiol Biomarkers Prev, 16 (4): 789-795, 2007.*
Bantis et al., Expression of p120, Ki-67 and PCNA as proliferation biomarkers in imprint smears of prostate, carcinoma and their prognostic value, Cytopathology, 2004, 15(1), p. 25-31.
Hickey, R.J., Malkas, R.H., Schnaper, L., 2006, Cspcna Isoform Antibodies and uses thereof CS-KEYS, Inc.
Qureshi, S.A., Bashir, M.U., Yaqinuddin, A., Utility of DNA methylation markers for diagnosing cancer, Int J Surg, 2010, 8(3), p. 194-8.
Dent, D., Liu, Z., Du, Y., Epigenetic alterations as cancer diagnostic, prognostic, and predictive biomarkers, Adv Genet, 2010, 71, p. 125-76.
Ahmed, H., Promoter Methylation in Prostate Cancer and its Application for the Early Detection of Prostate Cancer Using Serum and Urine Samples, Biomark Cancer, 2010, 2010(2), p. 17-33.
O'Day, E., Lal, A., MicroRNAs and their target gene networks in breast cancer, Breast Cancer Res, 2010, 12(2), p. 201.
Lin, P.Y., Yu, S.L, Yang, P.C., MicroRNA in lung cancer, Br J Cancer, 2010, 103(8), p. 1144-8.
Mascaux et al., Early detection and screening of lung cancer, Expert Review of Molecular Diagnostics, 2010, 10(6) p. 799-815.
Molina et al., Tumor markers (CEA, CA 125, CYFRA 21-1, SCC and NSE) in patients with non-small cell lung cancer as an aid in histological diagnosis and prognosis. Comparison with the main clinical and pathological prognostic factors, Tumour Biol, 2003, 24(4), p. 209-18.
Pavicevic et al., CYFRA 21-1 in non-small cell lung cancer—standardisation and application during diagnosis, Coll Antropol, 2008, 32(2), p. 485-98.
Huhtinen et al., Serum HE4 concentration differentiates malignant ovarian tumours from ovarian endometriotic cysts, Br J Cancer, 2009, 100(8), p. 1315-9.
Hellstrom et al., The HE4 (WFDC2) Protein Is a Biomarker for Ovarian Carcinoma, Cancer Res, 2003, 63(13): p. 3695-700.
Shirodkar, S.P., Lokeshwar, V.B., Potential new urinary markers in the early detection of bladder cancer, Curr Opin Urol, 2009, 19(5): p. 488-93.
Vrooman, O.P., Witjes, J.A., Urinary Markers in Bladder Cancer, Eur Urol, 2008, 53(5): p. 909-16.
Volpe et al., Bladder tumor markers: a review of the literature, Int J Biol Markers. 2008, 23(4): p. 249-61.
Shariat, S.F., Karam, J.A., Lerner, S.P., Molecular markers in bladder cancer, Curr Opin Urol, 2008, 18(1): p. 1-8.
Kapila et al., Could nuclear matrix protein 22 (NMP22) play a role with urine cytology in screening for bladder cancer?—experience at Kuwait University, Cytopathology. Dec. 2008;19(6): p. 369-74.
Morrissey et al., Urinary biomarkers for the early diagnosis of kidney cancer, Mayo Clin Proc, 2010, 85(5): p. 413-21.
Walgenbach-Brunagel et al., The use of a colon cancer associated nuclear antigen CCSA-2 for the blood based detection of colon cancer, J Cell Biochem. 2008, 104(1): p. 286-94.
Leman et al., Evaluation of colon cancer-specific antigen 2 as a potential serum marker for colorectal cancer, Clin Cancer Res. 2008, 14(5): p. 1349-54.
Leman et al., Initial analyses of colon cancer-specific antigen (CCSA)-3 and CCSA-4 as colorectal cancer-associated serum markers, Cancer Res. 2007, 67(12): p. 5600-5.

(Continued)

*Primary Examiner* — Jon P Weber
*Assistant Examiner* — Chunyuan Luo
(74) *Attorney, Agent, or Firm* — Bryan Cave LLP (57) ABSTRACT

The present invention relates to a method of detecting the presence of cancer by measuring the level of enzyme activity and autoantibodies in the blood of an individual. In particular the present invention relates to methods for measurement of activated cAMP-dependent protein kinase A (PKA) activity and antibodies to PKA, a kit for activated PKA activity measurement, and the use of the measured levels of these analytes for determining the presence of cancer.

12 Claims, 4 Drawing Sheets

OTHER PUBLICATIONS

Gold et al., PAM4-reactive MUC1 is a biomarker for early pancreatic adenocarcinoma, Clin Cancer Res. 2007, 13 (24): p. 7380-7.

Gold et al., Characterization of monoclonal antibody PAM4 reactive with a pancreatic cancer mucin, Int J Cancer. 1994, 57(2): p. 204-10.

Gold et al., New MUC1 Serum Immunoassay Differentiates Pancreatic Cancer From Pancreatitis, J Clin Oncol, 2006, 24(2): p. 252-8.

Schilling et al., The Prostate Cancer gene 3 assay: indications for use in clinical practice, BJU Int. 2010, 105(4): p. 452-5.

Groskopf et al., APTIMA PCA3 molecular urine test: development of a method to aid in the diagnosis of prostate cancer, Clin Chem. 2006, 52(6): p. 1089-1095.

de Kok et al., DD3(PCA3), a very sensitive and specific marker to detect prostate tumors, Cancer Res. 2002, 62(9): p. 2695-2698.

Mao et al., Golgi protein 73 (GOLPH2) is a valuable serum marker for hepatocellular carcinoma, Gut. 2010, 59(12): p. 1687-1693.

Marrero et al., GP73, a resident Golgi glycoprotein, is a novel serum marker for hepatocellular carcinoma, J Hepatol. 2005, 43(6): p. 1007-1012.

Rollins, G., PSA Testing: Yes, No, Maybe? Clin Lab News, 2009, 35(6): p. 1, 3-5.

Smith, D.S., Humphrey, P.A., Catalona, W.J. The early detection of prostate carcinoma with prostate specific antigen: the Washington University experience, Cancer. 1997, 80(9): p. 1852-1856.

Schroder et al., Screening and Prostate-Cancer Mortality in a Randomized European Study, N Engl J Med 2009, 360: p. 1320-1328.

Elmore et al., Screening for breast cancer, JAMA. 2005, 293(10): p. 1245-1256.

Subramanian, S., Bobashev, G., Morris R.J., Modeling the cost-effectiveness of colorectal cancer screening: policy guidance based on patient preferences and compliance, Cancer Epidemiol Biomarkers Prev. 2009, 18(7): p. 1971-8.

Yurkovetsky et al., Development of a multimarker assay for early detection of ovarian cancer, J Clin Oncol. 2010, 28(13): p. 2159-66.

Gnjatic et al., Seromic profiling of ovarian and pancreatic cancer, Proc Natl Acad Sci U S A. 2010, 107(11): p. 5088-93.

Farlow et al., Development of a multiplexed tumor-associated autoantibody-based blood test for the detection of non-small cell lung cancer, Clin Cancer Res. 2010, 16(13): p. 3452-62.

Donach et al., Combined use of biomarkers for detection of ovarian cancer in high-risk women, Tumour Biol. 2010, 31(3): p. 209-15.

Chen et al., Autoantibodies to tumor-associated antigens combined with abnormal alpha-fetoprotein enhance immunodiagnosis of hepatocellular carcinoma, Cancer Lett. 2010, 289(1): p. 32-9.

Chan et al., Multiple serological biomarkers for colorectal cancer detection, Int J Cancer. 2010, 126(7): p. 1683-90.

Talesa et al., Diagnostic potential in prostate cancer of a panel of urinary molecular tumor markers, Cancer Biomark. 2009, 5(6): p. 241-51.

Nosov et al., Validation of serum biomarkers for detection of early-stage ovarian cancer, Am J Obstet Gynecol. 2009, 200(6): p. 639 e1-5.

Amonkar et al., Development and preliminary evaluation of a multivariate index assay for ovarian cancer, PLoS One. 2009, 4(2): p. e4599.

Zhong et al., Autoantibodies as potential biomarkers for breast cancer, Breast Cancer Res. 2008, 10(3): p. R40.

Ran et al., Profiling tumor-associated autoantibodies for the detection of colon cancer, Clin Cancer Res. 2008, 14(9): p. 2696-700.

Ludwig et al., Pattern of serum autoantibodies allows accurate distinction between a tumor and pathologies of the same organ, Clin Cancer Res. 2008, 14(15): p. 4767-74.

Clark et al., Performance of a single assay for both type III and type VI TMPRSS2:ERG fusions in noninvasive prediction of prostate biopsy outcome, Clin Chem. 2008, 54(12): p. 2007-17.

Zheng et al., A multiparametric panel for ovarian cancer diagnosis, prognosis, and response to chemotherapy, Clin Cancer Res. 2007, 13(23): p. 6984-92.

Patz et al., Panel of serum biomarkers for the diagnosis of lung cancer, J Clin Oncol. 2007, 25(35): p. 5578-83.

Lopez-Casas, P.P., Lopez-Fernandez, L.A., Gene-expression profiling in pancreatic cancer, Expert Rev Mol Diagn. 2010, 10(5): p. 591-601.

Dsouza et al., Collagen-induced morphogenesis and expression of the A2-integrin subunit is inhibited in c:erhB2-transfected human mammary epithelial cells, Oncogene 1993, 8, 1797-1806.

Batra et al., Expression of the human MUC1 mucin cDNA in a hamster pancreatic tumor cell line HP-1, International Journal of Pancreatology, DOI: 10.1007/BF02924367, 1992, 12, 271-283.

Blackwood et al., Functional Analysis of the AUG- and CUG-Initiated Forms of the c-Myc Protein, Molecular Biology of the Cell 1994, 5, 597-609.

Matlashewski et al., Isolation and characterization of a human p53 cDNA clone: expression of the human p53 gene, EMBO J. 1984, 3(13), 3257-3262.

Wolf et al., In Vitro Expression of Human p53 cDNA Clones and Characterization of the Cloned Human p53 Gene, Molecular and Cellular Biology 1985, 5(8), 1887-1893.

Capella et al., Frequency and Spectrum of Mutations at Codons 12 and 13 of the C-K-ras Gene in Human Tumors, Environ. Health Perspectives 1991, 93, 125-131.

Scully et al, BRCA1 is a component of the RNA polymerase II holoenzyme, PNAS 1997, 94, 5605-10.

Sharan et al., Embryonic lethality and radiation hypersensitivity mediated by Rad51 in mice lacking Brca2, Nature 386, 1997, 804-810.

Su et al., Cancer Res. 1993, 53, 2727-2731.

Munemitsu et al., Regulation of intracellular B-catenin levels by the adenomatous Regulation of intracellular B-catenin levels by the adenomatous polyposis coli (APC) tumor-suppressor protein, PNAS 1995, 92, 3046-50.

Nouwen et al., Occurrence of the mucinous differentiation antigen CA12S in genital tract and conductive airway epithelia of diverse mammalian species (rabbit, dog, monkey), Differentiation 1990, 45, 192-8.

Rosenberg et al., Biochem Biophys Res Commun. 1998, 248, 935-939.

Zimmerman, A.L., Wu, S., MicroRNAs, cancer and cancer stem cells, Cancer Lett. 2011, 300(1): p. 10-9.

Taberlay, P.C., Jones, P.A., DNA methylation and cancer. Prog Drug Res. 2011, 67: p. 1-23.

Farazi et al., miRNAs in human cancer, J. Pathoi, 2011, 223(2): p. 102-15.

Wang, D., Dubois, R.N., Eicosanoids and Cancer, Nat. Rev. Cancer, 2010, 10(3): p. 181-93.

Theocharis et al., Proteoglycans in health and disease: novel roles for proteoglycans in malignancy and their pharmacological targeting, FEBS J, 2010, 277(19): p. 3904-23.

Taby, R., Issa, J.P., Cancer epigenetics, CA Cancer J Clin, 2010, 60(6): p. 376-92.

Silvera, D., Formenti, S.C., Schneider, R.J., Translational control in ancer, Nat. Rev. Cancer, 2010, 10(4): p. 254-66.

Shivapurkar, N., Gazdar, A.F., DNA methylation based biomarkers in non-invasive cancer screening, Curr Mol Med, 2010, 10(2): p. 123-32.

Lechner, M., Boshoff, C., Beck, S., Cancer epigenome, Adv genet, 2010, 70, p. 247-76.

Kosaka, N. Iguchi, H., Ochiya, T., Circulating microRNA in body fluid: A new potential biomarker for cancer diagnosis and prognosis, Cancer Sci, 2010, 101(10): p. 2087-92.

Khabar, K.S., Post-transcriptional control during chronic inflammation and cancer: a focus on AU-rich elements, Cell Mol Life Sci, 2010, 67(17): p. 2937-55.

Chen et al., Microfluidic isolation and transcriptome analysis of serum microvesicles, Lab Chip, 2010, 10(4): p. 505-11.

Bozza, P.T., Viola, J.P., Lipid droplets in inflammation and cancer, Prostaglandins Leukot Essent Fatty Acids, 2010, 82(4-6): p. 243-50.

Boffetta, P., Biomarkers in cancer epidemiology: an integrative approach, Carcinogenesis, 2010, 31(1): p. 121-6.

Bell, D.W., Our changing view of the genomic landscape of cancer, J Pathol, 2010, 220(2): p. 231-43.

Smith et al., Trans-fatty acids and cancer: a mini-review, Br J Nutr, 2009, 102(9): p. 1254-66.

Sequist et al., The CTC-Chip: The CTC-chip an exciting new tool to detect circulating tumor cells in lung cancer patients, J Thorac Oncol, 2009, 4(3): p. 281-3.

Fernandis, A.Z., Wenk, M.R., Lipid-based biomarkers for cancer, J Chromatogr B Analyt Technol Biomed Life Sci, 2009, 877(26): p. 2830-5.

Wang et al., Gene expression profiles and prognostic markers for primary breast cancer, Methods Mol Biol, 2007, 377: p. 131-8.

Masters, J.R., Clinical applications of expression profiling and proteomics in prostate cancer, Anticancer Res., 2007, 27(3A), p. 1273-6.

Pearce, L.R., Komander, D., Alessi, D.R., The nuts and bolts of AGC protein kinases, Nat Rev Mol Cell Biol. 2010, 11(1): p. 9-22.

Walsh et al., The inhibitor protein of the cAMP-dependent protein kinase, in peptides and protein phosphorylation, B. E. Kemp, Editor, 1990, CRC Press, Inc.: Boca Raton, FL p. 43-84.

Cho, Y.S., Lee, Y.N., Cho-Chung, Y.S., Biochemical characterization of extracellular cAMP-dependent protein kinase as a tumor marker, Biochem Biophys Res Commun. 2000, 278(3): p. 679-84.

Cho et al., Extracellular protein kinase a as a cancer biomarker: its expression by tumor cells and reversal by a myristate-lacking Calpha and RIIbeta subunit overexpression, Proc Natl Acad Sci USA, 2000, 97(2): p. 835-40.

Kerber et al., The new DR-70 immunoassay detects cancer of the gastrointestinal tract: a validation study, Aliment Pharmacol Ther, 2004, 20(9): p. 983-7.

Ward et al., Detection of pancreatic adenocarcinoma using circulating fragments of fibrinogen, Eur J Gastroenterol Hepatol, 2010, 22(11): p. 1358-63.

Wu et al., Clinical performance of the AMDL DR-70 immunoassay kit for cancer detection, J Immunoassay, 1998, 19(1): p. 63-72.

Stoimenov, I., Helleday, T., PCNA on the crossroad of cancer, Biochem Soc. Trans, 2009, 37(Pt 3): p. 605-13.

Czyzewska et al., Immunohistochemical evaluation of Ki-67, PCNA and MCM2 proteins proliferation index (PI) in advanced gastric cancer, folia histochem cytobiol, 2009, 47(2): p. 289-96.

Venturi et al., Human hepatocellular carcinoma expresses specific PCNA isoforms: an in vivo and in vitro evaluation, Lab Invest, 2008, 88(9): p. 995-1007.

Simionescu et al., P53 and PCNA immunoexpression in endometrial carcinomas, Rom J Morphol Embryol, 2006, 47(2): p. 137-41.

Mun et al., Proliferating cell nuclear antigen (PCNA) activity in hepatocellular carcinoma, begine peri-neoplastic and normal liver, Malays J Pathol, 2006, 28(2): p. 73-7.

Malkas et al., A cancer-associated PCNA expressed in breast cancer has implications as a potential biomarker, Proc Natl Acad Sci USA, 2006, 103(51): p. 19472-7.

Lyzogubov et al., Immunochistochemical analysis of Ki-67, PCNA and S6K1/2 expression in human breast cancer, Exp Oncol, 2005, 27(2): p. 141-4.

Proniewska-Skreted et al., Expression of PCNA and Ki-67 in posterior uveal melanomas in adults, Rocz Akad Med Bialymst, 2004, 49 Suppl 1, p. 79-81.

Kushlinskii et al., Expression of biomolecular markers (Ki-67, PCNA, Bcl-2, BAX, BclX, VEGF) in breast tumors, Bull Exp Bio Med, 2004, 137(2), p. 182-5.

Czyzewska et al., Evaluation of proliferating markers Ki-67, PCNA in gastric cancers, Rocz Akad Med Bialymst, 2004, 49 Suppl 1, p. 64-6.

Bertucci et al., Gene expression profiling of inflammatory breast cancer, Cancer. 2010, 116(11 Suppl): p. 2783-93.

Nannini et al., Gene expression profiling in colorectal cancer using microarray technologies: results and perspectives, Cancer Treat Rev. 2009, 35(3): p. 201-9.

Konstantinopoulos, P.A., Spentzos, D., Cannistra, S.A., Gene-expression profiling in epithelial ovarian cancer, Nat Clin Pract Oncol. 2008, 5(10): p. 577-87.

Cheang, M.C., van de Rijn, M., Nielsen, T.O., Gene expression profiling of breast cancer, Annu Rev Pathol. 2008, 3: p. 67-97.

Arslan et al., Use of CA15-3, CEA and prolactin for the primary diagnosis of breast cancer and correlation with the prognostic factors at the time of initial diagnosis, Ann Nucl Med. 2000, 14(5): p. 395-9.

Hou et al., Evaluation of serum CA27.29, CA15-3 and CEA in patients with breast cancer, Kaohsiung J Med Sci. 1999, 15(9): p. 520-8.

Hayes, D.F., Zurawski, Jr. V.R., Kufe, D.W., Comparison of circulating CA15-3 and carcinoembryonic antigen levels in patients with breast cancer, J Clin Oncol. 1986, 4(10): p. 1542-50.

Harris et al., American Society of Clinical Oncology 2007 update of recommendations for the use of tumor markers in breast cancer, J Clin Oncol. 2007, 25(33): p. 5287-312.

Duffy et al., Tumour markers in colorectal cancer: European Group on Tumour Markers (EGTM) guidelines for clinical use, Eur J Cancer. 2007, 43(9): p. 1348-60.

Suh et al., Ovarian cancer biomarkers for molecular biosensors and translational medicine, Expert Rev Mol Diagn. 2010, 10(8): p. 1069-83.

Ren et al., Tumor markers for early detection of ovarian cancer, Expert Rev Mol Diagn. 2010, 10(6): p. 787-98.

Moore et al., A novel multiple marker bioassay utilizing HE4 and CA125 for the prediction of ovarian cancer in patients with a pelvic mass, Gynecol Oncol. 2009, 112(1): p. 40-6.

Huerta, S., Recent advances in the molecular diagnosis and prognosis of colorectal cancer, Expert Rev Mol Diagn. 2008, 8(3): p. 277-88.

Jemal et al., Cancer statistics, 2009, CA Cancer J Clin. 2009, 59(4): p. 225-49.

Jemal et al., Cancer statistics, 2009, CA Cancer J Clin. 2009: p. caac.20006.

Wahls, T.L., Peleg, I., Patient- and system-related barriers for the earlier diagnosis of colorectal cancer, BMC Fam Pract. 2009, 10: p. 65.

Smith et al., Future of cancer incidence in the United States: burdens upon an aging, changing nation, J Clin Oncol. 2009, 27(17): p. 2758-65.

Lodde, M., Fradet, Y., The detection of genetic markers of bladder cancer in urine and serum, Curr Opin Urol. 2008, 18(5): p. 499-503.

Patent Cooperation Treaty, International Search Report for PCT/US2010/052597, issued Mar. 15, 2011, 3 pages.

Patent Cooperation Treaty, International Search Report for PCT/US20112/034049, issued Nov. 29, 2012, 4 pages.

Patent Cooperation Treaty, International Search Report for PCT/US2012/034080, issued Nov. 30, 2012, 6 pages.

Cho-Chung, et al., The regulatory subunit of cAMP-dependent protein kinase as a target for chemotherapy of cancer and other cellular dysfunctional-related diseases, Pharmac. Thera., 1993, 60: p. 265-288.

* cited by examiner

MEASUREMENT OF PKA FOR CANCER DETECTION

TECHNICAL FIELD

The present invention is in the field of diagnostics and relates to methods for determining the presence, activity, and concentrations of certain protein biomarkers and their use in determining the presence of cancer.

BACKGROUND ART

This application claims priority of US provisional patent 61251769 filed on Oct. 15, 2009.

The cAMP-dependent protein kinase (PKA) is activated by the binding of cAMP to the regulatory subunit (R), of the molecule and results in the release of the active catalytic kinase subunit (C). Most of the effects of cAMP in eukaryotic systems are the result of phosphorylation of proteins at serine or threonine residues by PKA. There are several isoforms of both subunits of PKA. PKA is localized subcellularly by binding to multidomain scaffolding proteins known as AKAPs which bind to the R subunits of the holoenzyme [1]. More than 50 AKAPs are known which localize PKA in various cell types. The PKA-specific inhibitor (PKI) acts by binding with high affinity to the substrate binding site of the free active catalytic subunit [2].

Work done at the National Cancer Institute (NCI) and by others showed that the activity level of PKA is elevated in the plasma of cancer patients, and that anti-PKA antibody levels are elevated in the serum of cancer patients [3-6]. Humphries et al demonstrated that oxidation of PKA inhibited its activity [7]. This inhibition could be overcome by the addition of the reducing agent dithiothreitol. Unexpectedly, the current invention shows that activated (reduced) PKA activity is low in plasma or serum of cancer patients relative to that of controls.

PSA Screening Test for Prostate Cancer

The PSA (prostate-specific antigen) blood test for prostate cancer is of questionable value as a screening test. In fact the American Cancer Society no longer recommends that men routinely have PSA tests as part of their routine physical examinations [8]. There are several reasons for this lack of support for testing. When prostate cancer is present, the PSA test fails to detect 3 out of 4 cases [9]. In addition, when the PSA test comes back positive, 3 out 4 times it is a false positive—the patient does not have cancer [10]. Nonetheless, patients who have a positive PSA test typically will have a group of 12 or more biopsy samples taken from their prostate to verify if cancer is present. At an average cost of $1,500 per biopsy, the national cost for the 700,000 unnecessary prostate biopsies done each year exceeds $1 billion [11]. Making matters worse, there is a 25% chance that a prostate biopsy will not detect cancer even when cancer is present [12]. Improved patient outcome could be accomplished by replacing a biopsy with a cancer confirmatory blood test, for a savings in health care costs of nearly $900 million annually.

Mammogram Screening Test for Breast Cancer

Mammograms have a poorer record than PSA tests. While mammograms are purported to detect 85-90% of breast cancers when they are present, the detected tumors on average are 1½ inches in diameter when diagnosed. As for all cancers, earlier detection leads to better patient outcomes. What makes breast cancer screening costly is that an estimated 95% of the positive mammograms are false positives—the patient does not have cancer [13]. A positive mammogram frequently leads to a breast biopsy. A typical needle biopsy costs about $1,500; an invasive surgical biopsy (about ⅓ of all breast biopsies) costs about $5,000. This brings the national cost for the estimated 2 million unnecessary breast biopsies to more than $5.1 billion annually. Improved patient outcome could be accomplished by substituting a cancer confirmatory test for a biopsy, for a savings in health care costs of almost $5 billion annually.

Cancer Monitoring Tests

Beyond screening tests there are additional blood tests that are used to monitor cancer patients once cancer has been diagnosed. Many of these tests are not specific for cancer or specific for a particular type of cancer, rendering them useless as cancer screening tests. However, they can be an effective means for monitoring cancer treatment and testing for disease recurrence. These tests include CA-15.3 and CA27.29 for breast cancer, CA 125 for ovarian cancer, CEA for colon cancer and PSA for prostate cancer [14]. Other blood tests have been used to determine if a primary cancer has spread to other organs. These tests include assays for metastases to bone (osteoprotegrin), and liver (E-selectin).

Work done at the National Cancer Institute (NCI) and by others taught that the activity level of PKA is elevated in the plasma of cancer patients, and that anti-PKA antibody levels are elevated in the serum of cancer patients [3-4].

SUMMARY OF INVENTION

A method is described for determining the presence of cancer in a patient consisting of measuring the activity of activated PKA in a patient sample serum or plasma and determining that the activity of activated PKA is lower than that of a control sample or control population.

In addition a method is provided wherein, in addition to measuring the level of activated PKA in the sample, the level of anti-PKA antibody also is measured. Elevated levels of anti-PKA antibody relative to a control sample or a control population plus low levels of activated PKA activity are used to determine the presence of cancer.

Also described is a method for determination of the levels of anti-PKA antibody in human serum or plasma wherein the difference in signal between PKA-coated and uncoated wells is used to correct for non-specific signal.

Lastly a kit is described for determining the amount of activated PKA activity in a sample.

Technical Problem

There is an important unmet need for non-invasive cancer screening tests and tests to verify the results of positive cancer screening tests. Additionally, better non-invasive tests are needed for determining the stage of cancer when diagnosed and for monitoring patient treatment and recovery. An estimated 1.4 million cases of cancer will be diagnosed in the U.S. this year [15]. As the population is aging the number of cancer cases is expected to increase by 19% [16-17]. Approximately 10.8 million people alive today have, or have had, diagnosed cancer [18]. Over 20 million individuals will be screened for breast or prostate cancer this year.

A blood test that confirmed, monitored or screened for all types of cancer would be of benefit. The test would serve as a universal confirmation test for presumptive positive PSA, Pap smear, and mammogram tests. Additionally it would be important if the test could determine the stage of diagnosed cancer and whether metastasis has occurred. Such a test could be used to monitor patient treatment, test for cancer recurrence, and it could be used by pharmaceutical companies to monitor the efficacy of cancer drugs under development.

Solution to the Problem

In contrast to what would be expected from the work of other investigators [3-4], we have shown that low levels of activated PKA activity are present in serum or plasma of cancer patients relative to the levels in control samples. This decrease in activity can be used to determine the presence of cancer in patients with breast, colorectal, lung, and prostate cancer. In these experiments oxidized PKA in the sample is activated by the inclusion of β-mercaptoethanol or a similar antioxidant in the reaction mixture. Results from such experiments are detailed below.

Advantageous Effects of Invention

Extremely low levels of PKA activity are detectable in non-reduced blood samples making accurate measurement of enzyme activity very difficult. The addition of an antioxidant to the PKA assay activates the enzyme making it much easier to measure the PKA activity and to measure differences, especially decreases, in enzyme activity. Assaying activated PKA activity in blood samples provides identification of individuals who have cancer by virtue of their low levels of activated PKA activity. The detection of elevated levels of anti-PKA antibodies in addition to measurement of low activated PKA activity provides additional evidence that individuals have cancer.

DESCRIPTION OF EMBODIMENTS

Embodiment 1

Serum samples from patients with early and late-stage cancer were obtained from ProMedDx, LLC. In one embodiment blood samples from prostate cancer patients and normal controls presumably without cancer were assayed for activated PKA activity. In this assay activated PKA in samples was mixed with a defined peptide used as a substrate. Phosphorylation of the peptide was detected using biotinylated phosphoserine antibody, which was in turn was detected in an ELISA format using peroxidase-conjugated to streptavidin. Detection of the bound peroxidase was established using a color-producing peroxidase substrate. Bovine PKA catalytic unit was used at varying concentrations to develop a standard activity curve. The detail of the assay protocol is described below.

Modified MESACUP Protein Kinase A Activity Assay
1. Reference: Kit Instructions
2. Materials
    a. MESACUP Protein Kinase Assay Kit (MBL Code No. 5230)
    b. ATP: 10 mM in water
        i. Dissolve 60 mg ATP (Sigma Prod. No. A2383) in 1.0 ml water
        ii. Determine the absorbance of a 1/1000 dilution in PBS at 259 nm
        iii. Store at −20° C.
        iv. Immediately before use dilute to 10 mM based on the absorbance and the molar extinction coefficient (E259, pH 7=15,400)
    c. PKI inhibitor: 0.5 mM in water (Santa Cruz Prod. No. sc-201160)
        i. Dissolve 1 mg in 1.0 ml water
        ii. Store at −20° C.
    d. PKA diluent: 25 mM KH2PO4, 5 mM EDTA, 150 mM NaCl, 50% (w/v) glycerol, 1 mg/ml BSA, 5 mM β-mercaptoethanol, pH 6.5
    e. PKA catalytic subunit standard:
        i. Dissolve bovine PKA (Sigma Prod. No. P2645) in cold PKA diluent to a final concentration of 1 µg/ml
        ii. Store at −20° C.
    f. Peroxidase substrate solution (Sigma Prod. No. T8665)
3. Procedure
    a. Prepare samples
        i. Thaw serum samples
        ii. Centrifuge 10 minutes at 16,000×g
        iii. Collect the clear supernatant
        iv. Mix 0.0108 ml supernatant with 0.0012 ml diluent in a dilution plate, two wells per sample
        v. Incubate one hour at room temperature
    b. Prepare calibration curve
        i. Prepare serial ½ dilutions of PKA 20-0.4 ng/ml in PKA diluent
        ii. Dispense 0.012 ml per well of a dilution plate
    c. Prepare reaction buffer to final concentrations of:
        i. 25 mM tris-HCl, pH 7.0
        ii. 3 mM MgCl2
        iii. 1 mM ATP
        iv. 0 or 0.5 uM PKI
    d. Add 0.108 ml reaction buffer (with or without PKI) to each sample or calibrator well of the dilution plate
    e. Pre-incubate five minutes at 25° C.
    f. Transfer 0.100 ml per well to assay plate
    g. Incubate 20 minutes at 25° C. with shaking at 750 rpm
    h. Add 0.100 ml kit stop solution per well
    i. Wash three times with kit wash buffer
    j. Add 0.100 ml kit biotinylated anti-phosphoserine per well
    k. Incubate 60 minutes at 25° C. with shaking at 750 rpm
    l. Wash three times with kit wash buffer
    m. Add 0.100 ml kit peroxidase-conjugated streptavidin per well
    n. Incubate 60 minutes at 25° C. with shaking at 750 rpm
    o. Wash three times with kit wash buffer
    p. Add 0.100 ml peroxidase substrate solution per well
    q. Incubate 60 minutes at 25° C. with shaking at 750 rpm
    r. Add 0.100 ml kit stop solution per well
    s. Shake briefly until well mixed
    t. Read absorbance at 450 nm 4. Calculation of Results
   a. Plot absorbance versus concentration of the calibration curve
   b. Perform a least squares linear regression on the data to determine the slope and intercept
   c. Calculate kinase concentration in the samples
      i. Kinase (ng/ml)=(sample absorbance−intercept)/slope
   d. Calculate net PKA in the samples
      i. Net PKA (ng/ml)=Kinase (0 μM PKI)−Kinase (0.5 μM PKI)

Figure 1:
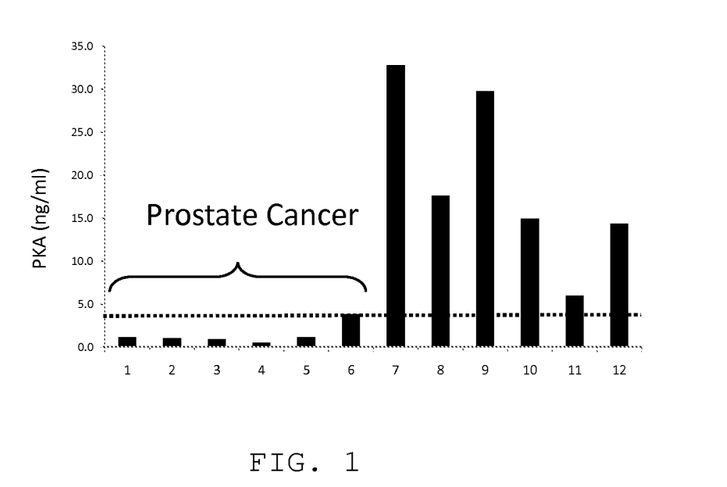
FIG. 1 is a bar graph of the levels of activity of activated PKA in prostate cancer patients relative to those of age and sex-matched normal controls.

The activity levels of activated PKA in blood from the prostate cancer patients were lower (below 4 ng/ml) compared to those for samples from age and sex-matched controls (FIG. 1).

Embodiment 2

Figure 2:
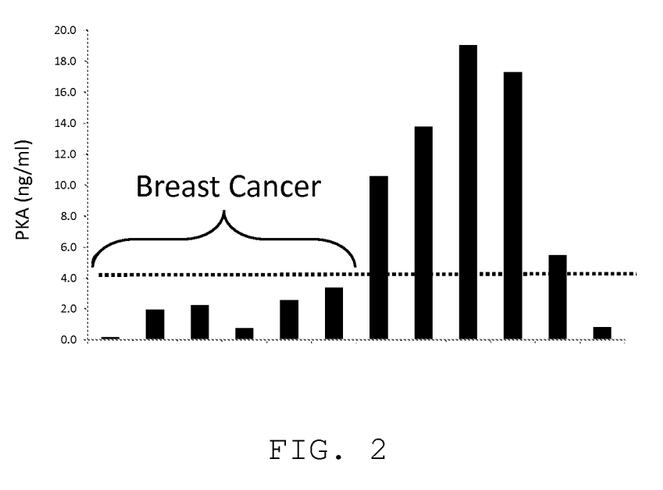
FIG. 2 is a bar graph of the levels of activity of activated PKA in prostate cancer patients relative to those of age and sex-matched normal controls.

Blood samples from breast cancer patients and from age and sex-matched normal controls presumably without cancer were analyzed for activated PKA activity using the same protocol as used in Embodiment 1. The activity levels of activated PKA in blood from breast cancer patients were lower (below 4 ng/ml) than those for samples from the normal controls (FIG. 2).

Embodiment 3

The same prostate cancer patient samples and related control samples used in Embodiment 1 were tested for anti-PKA antibodies as described below.
   PKA Autoantibody ELISA
   1. Materials
   a. MaxiSorp 96 well polystyrene plates (NUNC Prod. No. 439454)
   b. PKA diluent: 25 mM KH 2P04, 5 mM EDTA, 150 mM NaCl, 50% (w/v) glycerol, 1 mg/ml BSA, 5 mM β-mercaptoethanol, pH 6.5
   c. Protein Kinase A (Sigma Prod. No. P2645)
      i. Dissolve in PKA diluent and dilute to 50 μg/ml
      ii. Store at −20° C.
   d. Coating buffer: 10 mM sodium phosphate, 150 mM sodium chloride, pH 7.4
   e. Coating wash buffer: 20 mM HEPES, 150 mM sodium chloride, 30 mM sucrose, pH 7.0 with 0.1% BSA
   f. Blocker Casein (Pierce Prod. No. 37532)
   g. Assay buffer: 10 mM sodium phosphate, 150 mM sodium chloride, pH 7.4 with 0.25% BSA and 0.1% Tween 20
   h. Assay wash buffer: 10 mM citrate, 150 mM sodium chloride, pH 5.1 with 0.1% Tween 20
   i. Detection antibody: peroxidase-conjugated donkey anti-human IgG (H+L) (Jackson Prod. No. 709-035-149), 0.8 mg/ml in 10 mM sodium phosphate, 250 mM sodium chloride, pH 7.6 with 15 mg/ml bovine serum albumin
   j. Stop solution: 0.2 M H2S04 in water
   k. HRP substrate solution (Sigma Prod. No. T8665)
   2. Procedure
   a. Prepare the assay plates
      i. Dilute PKA to 0.5 μg/ml in coating buffer (+PKA wells)
      ii. Dilute PKA diluent 1/100 in coating buffer (−PKA wells)
      iii. Add 0.100 ml either +PKA or −PKA solution per well
      iv. Seal and incubate overnight at 4° C.
      v. Aspirate to remove the coating solutions
      vi. Add 0.200 ml blocking solution per well
      vii. Incubate one hour at room temperature
      viii. Wash three times with coating wash buffer
      ix. Use immediately
   b. Prepare samples
      i. Thaw serum samples
      ii. Centrifuge 10 minutes at 16,000×g
      iii. Collect the clear supernatant
      iv. Dilute 1/500 in assay buffer
   c. Add 0.100 ml diluted sample each to the +PKA and −PKA wells
   d. Incubate two hours at 25° C. with shaking at 750 rpm
   e. Wash three times with assay wash buffer
   f. Dilute the detection antibody 1/20,000 in assay buffer
   g. Add 0.100 ml per well
   h. Incubate one hour at 25° C. with shaking at 750 rpm
   i. Wash three times with assay wash buffer
   j. Add 0.100 ml HRP substrate solution per well
   k. Incubate 20 minutes at 25° C. with shaking at 750 rpm
   l. Add 0.100 ml stop solution per well
   m. Shake briefly until well mixed
   n. Read absorbance at 450 nm
   3. Calculation of results
   a. Calculate net anti-PKA signal in the samples
      i. Net anti-PKA=Absorbance (+PKA)−Absorbance (−PKA)

Figure 3:
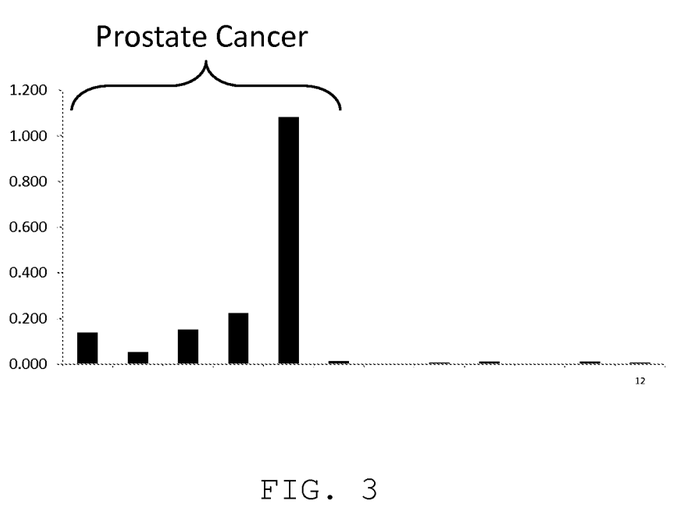
FIG. 3 is a bar graph of the levels of anti-PKA antibody in serum relative to the levels of activated PKA activity.

The levels of anti-PKA antibodies in the prostate cancer patient serum relative to the levels of activated PKA activity (anti-PKA antibody/activated PKA activity) were higher than those for samples from age and sex-matched controls (FIG. 3). The activated PKA activities for these samples also were low relative to those of matched controls (FIG. 1). These observations using the same samples used in Embodiment 1 indicate that the results of both assays together can be used to detect the presence of cancer.

Embodiment 4

Figure 4:
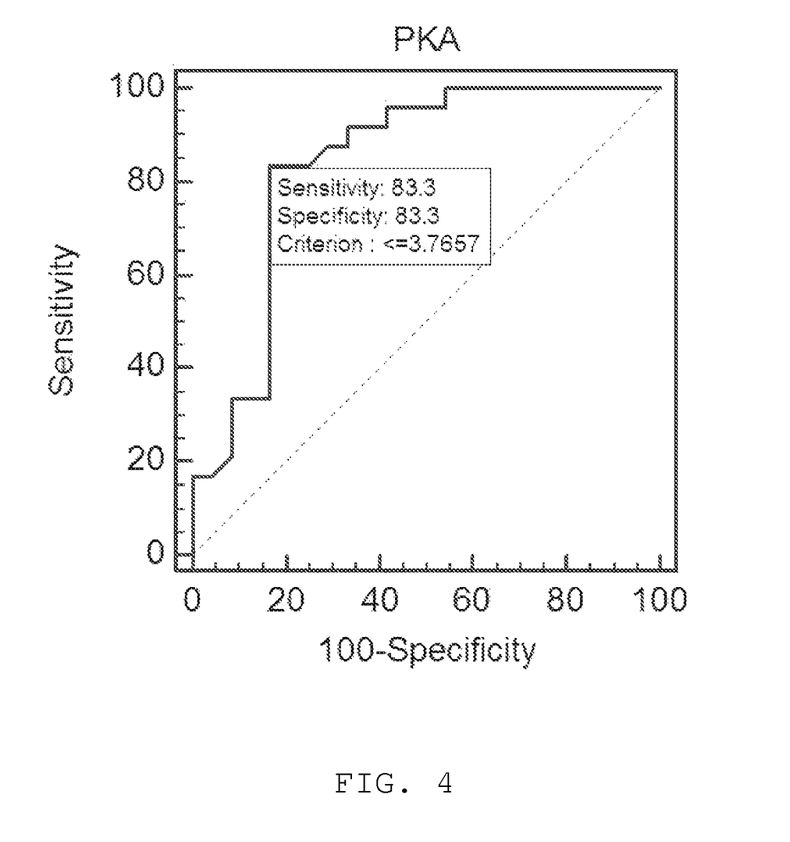
FIG. 4 is a receiver operating characteristic (ROC) plot of the levels of activated PKA activity in serum from cancer patients and from age and sex-matched controls.

In this embodiment blood samples from 24 patients with prostate, breast, colon, or lung cancer and 24 age- and sex-matched normal controls presumably without cancer were assayed for activated PKA activity. Twenty of twenty-four cancer patients had low activated PKA activity, while twenty of twenty-four normal controls had high activity. The calculated sensitivity of the assay was 0.83 and the assay specificity was 0.83. Receiver operating characteristic analysis of the results indicated that there was a 0.833 correlation of low activated PKA activity with the presence of cancer at a cutoff value of 3.8 ng/ml of activated PKA activity (FIG. 4).

INDUSTRIAL APPLICABILITY

The measurement of the levels of activated PKA activity can be used to determine the presence of cancer in individuals. In addition the measurement of levels of activated PKA activity and anti-PKA antibody can be used together to indicate the presence of cancer in individuals.

REFERENCE SIGNS LIST

Citation List

1. Pearce, L. R., D. Komander, and D. R. Alessi, *The nuts and bolts of AGC protein kinases. Nat Rev Mol Cell Biol,* 2010. 11 (1): p. 9-22.
2. Walsh, O. A, et al, *The inhibitor protein of the cAMP-dependent protein kinase,* in Peptides and Protein Phosphorylation, B. E. Kemp, Editor. 1990, CRC Press, Inc.: Boca Raton, Fla. p. 43-84.

3. Cho, Y. S., Y. N. Lee, and Y. S. Cho-Chung, *Biochemical characterization of extracellular cAMP-dependent protein kinase as a tumor marker.* Biochem Biophys Res Commun, 2000. 278(3): p. 679-84.
4. Cho, Y. S., et al, *Extracellular protein kinase A as a cancer biomarker: its expression by tumor cells and reversal by a myristate-lacking Calpha and RIIbeta subunit overexpression.* Proc Natl Acad Sci USA, 2000. 97(2): p. 835-40.
5. Nesterova, M. V., et al, *Autoantibody cancer biomarker: extracellular protein kinase A.* Cancer Res, 2006. 66(18): p. 8971-4.
6. Cho-Chung, Y. S. and C. Chung, *Autoantibody detection for cancer diagnostics* 2005, Govt. of the U.S. of America: United States.
7. Humphries, K. M., C. Juliano, and S. S. Taylor, *Regulation of cAMP-dependent protein kinase activity by glutathionylation.* J Bioi Chem, 2002. 277(45): p. 43505-11.
8. Rollins, G., *PSA Testing: Yes, No, Maybe.* Clin Lab News, 2009. 35(6): p. 1, 3-5.
9. Smith, O. S., P. A Humphrey, and W. J. Catalona, *The early detection of prostate carcinoma with prostate specific antigen: the Washington University experience.* Cancer, 1997. 80(9): p. 1852-6.
10. Schroder, F. H., et al, *Screening and prostate-cancer mortality in a randomized European study.* N Engl J Med, 2009. 360(13): p. 1320-8.
11. Jemal, A, et al, *Cancer Statistics,* 2008. CA Cancer J Clin, 2008. 58(2): p. 71-96.
12. Ahmed, H. U., et al, *Is it time to consider a role for MRI before prostate biopsy?* Nat Rev Clin Oncol, 2009. 6(4): p. 197-206.
13. Elmore, J. G., et al, *Screening for Breast Cancer.* JAMA, 2005. 293(10): p. 1245-1256.
14. Harris, L., et al, *American Society of Clinical Oncology 2007 update of recommendations for the use of tumor markers in breast cancer.* J Clin Oncol, 2007. 25(33): p. 5287-312.
15. Jemal, A, et al, *Cancer Statistics,* 2009. CA Cancer J Clin, 2009: p. caac.20006.
16. Boudreau, A C., et al, *Signaling pathway adaptations and novel protein kinase A substrates related to behavioral sensitization to cocaine.* J Neurochem, 2009. 110(1): p. 363-77.
17. Smith, B. D., et al, *Future of cancer incidence in the United States: burdens upon an aging, changing nation.* J Clin Oncol, 2009. 27(17): p. 2758-65.
18. *American Cancer Society. Cancer Facts & Figures* 2008. 2008, American Cancer Society: Atlanta.

The invention claimed is:

1. A method for determining the presence of cancer in a patient comprising (i) incubating a sample of the patient's serum or plasma with a reducing agent to activate PKA in the sample, (ii) measuring the activity of the activated PKA and (iii) determining that the activity of the activated PKA is lower than the activity of activated PKA of a control sample or control population presumably without cancer.

2. The method of claim 1 wherein the method further comprises measuring the level of anti PKA antibody determining that the level of anti-PKA antibody is elevated relative to a control sample or control population presumably without cancer.

3. The method of claim 2 wherein the method is a method for determining the presence of breast, colorectal, lung or prostate cancer.

4. The method of claim 2 wherein the method is a method for determining the presence of breast or prostate cancer.

5. The method of claim 2 wherein the method is a method for determining the presence of breast cancer.

6. The method of claim 2 wherein the method is a method for determining the presence of prostate cancer.

7. The method of claim 2 wherein the reducing agent is β-mercaptoethanol.

8. The method of claim 1 wherein the method is a method for determining the presence of breast, colorectal, lung or prostate cancer.

9. The method of claim 1 wherein the method is a method for determining the presence of breast or prostate cancer.

10. The method of claim 1 wherein the method is a method for determining the presence of breast cancer.

11. The method of claim 1 wherein the method is a method for determining the presence of prostate cancer.

12. The method of claim 1 wherein the reducing agent is β-mercaptoethanol.

* * * * *